US007010962B2

(12) United States Patent
Sinha (10) Patent No.: US 7,010,962 B2
(45) Date of Patent: Mar. 14, 2006

(54) CHARACTERIZATION OF LIQUIDS USING GAS BUBBLES

(76) Inventor: Naveen N. Sinha, 112 Shirlane Pl., Los Alamos, NM (US) 87544

( * ) Notice: Subject to any disclaimer, the term of this patent is extended or adjusted under 35 U.S.C. 154(b) by 116 days.

(21) Appl. No.: 10/752,328

(22) Filed: Jan. 5, 2004

(65) Prior Publication Data

US 2004/0144175 A1    Jul. 29, 2004

Related U.S. Application Data

(60) Provisional application No. 60/442,281, filed on Jan. 24, 2003.

(51) Int. Cl.
*A61B 8/00* (2006.01)
*G01N 13/00* (2006.01)
(52) U.S. Cl. .................. 73/54.15; 73/54.24; 73/64.53; 73/602; 73/579; 600/438; 600/443
(58) Field of Classification Search .......... 73/597–600, 73/601–602, 606, 627–628, 632, 643, 620, 73/625, 626; 600/407, 439, 443; 601/2
See application file for complete search history.

(56) References Cited

U.S. PATENT DOCUMENTS

| | | | | |
|---|---|---|---|---|
| 3,640,271 A | * | 2/1972 | Horton | 600/438 |
| 4,069,468 A | * | 1/1978 | Bartram | 367/91 |
| 4,265,251 A | * | 5/1981 | Tickner | 600/438 |
| 4,483,345 A | * | 11/1984 | Miwa | 600/438 |
| 5,749,364 A | * | 5/1998 | Sliwa | 600/438 |
| 6,085,577 A | * | 7/2000 | Christensen et al. | 73/64.51 |
| 6,322,512 B1 | * | 11/2001 | De Jong et al. | 600/458 |

FOREIGN PATENT DOCUMENTS

| | | | |
|---|---|---|---|
| JP | 11153582 A | * | 6/1999 |
| WO | WO 99/47045 | * | 9/1999 |

OTHER PUBLICATIONS

T.G. Leighton, "The Acoustic Bubble." (Academic Press, London, 1994) pp. 119-207.
H.C. Pumphrey and A.J. Walton, "Experimental study of the sound emitted by water drops impacting on a water surface." European Journal of Physics, 9(3), pp. 225-231 1988.

(Continued)

*Primary Examiner*—Hezron Williams
*Assistant Examiner*—Rose M. Miller
(74) *Attorney, Agent, or Firm*—Samuel M. Freund; Cochran Freund & Young LLC (57) ABSTRACT

An apparatus and method is described for measuring properties of bubbles from which certain physical characteristics of the liquid in which the bubbles are generated can be determined. The evolution of a bubble includes (1) formation and growth at a nozzle disposed within the liquid through which a gas is flowed, or formation and growth as a result of cavitation in the liquid from the application of focused acoustic energy to a location within the liquid; (2) detachment and resonance; and (3) rise towards terminal velocity. Measurements of the resonance frequency, the shape oscillation frequency and the terminal velocity of the bubble allow the determination of the density and surface tension of the liquid and the radius of the bubble. Since the properties of the liquid affect the evolution of the bubble, observation of a rising bubble can be used as a tool for characterizing the liquid; as an example, the present invention can be used to monitor changes in the liquid itself or changes in the concentration or integrity of materials dissolved in the liquid.

43 Claims, 10 Drawing Sheets

OTHER PUBLICATIONS

P. Di Marco, W. Grassi, G. Memoli. 37 Experimental study on terminal velocity of nitrogen bubbles in FC-72, Proc. Experimental Heat Transfer, Fluid Mechanics and Thermodyamics 2001, ed. by G.P. Celata, P. Di Marco, A. Goulas, and A. Mariana, Thessalonki, GR, Sep. 24-28, 2001, ETS pp. 1349-1359.

R. Mahalingam, R.S. Limaye and J.A. Brink Jr., "Velocity measurements in two-phase bubble-flow regime with laser-doppler anemometry." Am. Inst. Chem. Eng. Jour. vol. 22 No. 6 pp. 1152-1155 (1976).

D.S. Hacker and F.D. Hussein. "The Application of a Laser-Schlieren Technigure to the Study of single Bubble Dynamics," Ind. Eng. Chem. Fund. 17(4) pp. 277-283 (1978).

A. Gelmetti, T. Bellini, P. Lago and M. Corti, "An optical interferometer for Gas Bubble measurements," Rev. Sci. Instrum. 67(10), 3564-3566 (1996).

L. Rovati, P. Lago, M. Corti, and C. Gomarasca "An optical interferometer for gas bubble measurements," 64(6) 1463-1467 (1993).

N. Abuaf, T. P. Feierabend, G.A. Zimmer and O.C. Jones Jr. "Radio-frequency probe for bubble size and velocity measurements." Rev. Sci. Instrum. 50(10) 1260-1263 (1979).

T.G. Leighton nad A.J. Walton. "An experimetal study of the sound emitted from gas bubbles in a liquid." European Journal of Physics, 8, 98-104, (1987).

R.Y. Nishi, "Ultrasonic detection of bubbles with Doppler flow transducers," Ultrasonics, 10, pp. 173-179 (1972).

H. Kellerman, K. Juttner, G. Kreysa. "Dynamic modelling of gas-hold-up in different electrolyte systems." Journal of App Electrochemistry, 28, pp. 311-319 (1998).

M.S. Longuet-Higgins, B.R. Kerman and K. Lunde, "The release of air bubbles from an underwater nozzle," Journal of Fluid Mechanics. 230 pp. 365-390 (1991).

M. Minnaert. "On Musical Air-Bubbles and the Sounds of Running Water," Philosophical Mag. 16. pp. 235-248 (1993).

L.S. Fan and K. Tsuchiya, Bubble Wake Dynamics in Liquids and Liquid-Solid Suspensions (Butterworth-Heinemann, Boston, 1990) pp. 39-47.

G. Bozzano and M. Dente. Shape and terminal velocity of single bubble motion: a noval approach; Computers & Chemistry Engineering. 25 (2001) pp. 571-576.

G. Ligar-Belair, R. Marchal, B. Robillard, T. Dambrouck, A. Maujean, M. Vignes-Adler, P. Leandet. "On velocity of expanding spherical gas bubbles rising in line in supersaturated hydroalcoholic solutions: application to bubble trains in carbonated beverages." Lagmuir, 16 pp. 1889-1895, (2000).

D.G.H. Andrews. "An expiriment to demonstrate the principles and processes involved in medical Doppler ultrasound." Physics Education. 35(5) pp. 350-353 (2000).

S. Qian, D. Chen. "Joint Time-Frequency Analysis" Prentice Hall PTR, Upper Saddle River, 1996. pp. 45-52.

Mendelson, H.D. "The Prediction of Bubble Terminal Velocities from Wave Theory." A.I.Ch.E. Journal vol. 13, No. 2. pp. 250-253.

Dickens, R. and Ridley, A. "Ultrasonic Detection of Bubbles in Fluids". BED-vol. 50, 2001. Bioengineering Conference. ASME 2001. pp. 727-728.

* cited by examiner

CHARACTERIZATION OF LIQUIDS USING GAS BUBBLES

RELATED CASES

The present application claims the benefit of Provisional Patent Application Ser. No. 60/442,281, for "Characterization of Liquids Using Gas Bubbles" filed on Jan. 24, 2003.

FIELD OF THE INVENTION

The present invention relates generally to characterization of liquids and, more particularly, to the determination of certain properties of a liquid by measuring characteristics of bubbles formed therein.

BACKGROUND OF THE INVENTION

The dynamics of gas bubbles in liquids has been studied using a variety of optical and acoustic techniques for industrial applications and for basic physics research. High-speed photography (See, e.g., T. G. Leighton, *The Acoustic Bubble*. (Academic Press, London, 1994), pp. 119–207; H. C. Pumphrey and A. J. Walton, "Experimental study of the sound emitted by water drops impacting on a water surface," European Journal of Physics, 9(3), 225–231 (1988); and P. Di Marco et al., "Experimental Study on Terminal Velocity of Nitrogen Bubbles" in FC-72, Proc. Experimental Heat Transfer, Fluid Mechanics and Thermodynamics 2001, ed. by G. P. Celata et al., GR, Sep. 24–28, 2001, ETS, Pisa, pp. 1349–1359.) is the most widely used technique, but requires complex image processing to extract quantitative information about bubble behavior. Laser Doppler anemometry (See, e.g., R. Mahalingam et al., "Velocity measurements in Two-Phase Bubble-Flow Regime with Laser-Doppler Anemometry," J. Am. Inst. Chem. Eng. 22, 1152–1155 (1976).) has been used to study bubble terminal velocity, and the laser-Schlieren (See, e.g., D. S. Hacker and F. D. Hussein, "The Application of a Laser-Schlieren Technique to the Study of Single Bubble Dynamics," Ind. Eng. Chem. Fund. 17(4), 277–283 (1978).) technique has been used to study bubble shape and terminal velocities. Optical interferometry (See, e.g., A. Gelmetti et al., "An optical interferometer for gas bubble measurements," Rev. Sci. Instrum. 67(10), 3564–3566 (1996); and L. Rovati et al., 64 (6), 1463–1467 (1993).) has found use in the study of bubble oscillations in a sound field. These optical techniques require both a transparent liquid and window access to the liquid through the container. Radio-frequency probes (See, e.g., N. Abuaf et al., "Radio-frequency probe for bubble size and velocity measurements," Rev. Sci. Instrum. 50(10), 1260–1263 (1979).) have also been used to investigate bubble size and terminal velocity. Passive listening (See, e.g., T. G. Leighton and A. J. Walton, "An experimental study of the sound emitted from gas bubbles in a liquid", Euro. J. Phys. 8, 98–104 (1987).) at acoustic frequencies is typically used to study bubble resonance. Ultrasonic pulsed Doppler procedures have been used for bubble detection (See, e.g., R. Y. Nishi, "Ultrasonic detection of bubbles with Doppler flow transducers," Ultrasonics, 10, 173–179 (1972).) and terminal velocity measurements (See, e.g., H. Kellerman et al., "Dynamic modeling of gas-hold-up in different electrolyte systems," J. Appl. Electrochem. 28, 311–319 (1998).). Typically, the above-mentioned techniques are used to study only one or two aspects of the behavior of bubbles.

There are three principal stages to the evolution of a gas bubble: (1) formation and growth at the tip of a nozzle located in a liquid; (2) detachment and resonance; and (3) ascent to terminal velocity.

In the first stage of evolution, the bubble grows to a specific size at the opening of the nozzle, the radius of the nozzle opening and the properties of the surrounding liquid determining the ultimate size of the bubble (See, e.g. M. S. Longuet-Higgins, B. R. Kerman, and K. Lunde, "The release of air bubbles from an underwater nozzle," J. Fluid Mech. 230 (1991) p365–390.) As the bubble pinches off and detaches from the nozzle, it resonates (breathing-mode) briefly at a natural frequency determined primarily by its radius and the liquid density. The frequency $f_0$ of this resonance oscillation was first calculated by M. Minnaert in "On Musical Air-Bubbles and the Sounds of Running Water," Phil. Mag. 16, 235–248 (1933) to be:

$$f_0 = \frac{1}{2\pi R_0}\sqrt{\frac{3\gamma p_0}{\rho}}, \qquad (1)$$

where $R_0$ is the radius of the bubble, $\gamma$ is the ratio of specific heat at constant pressure to the specific heat at constant volume of the gas, $p_0$ is the hydrostatic pressure of surrounding liquid, and $\rho$ is the liquid density. This equation is reasonably accurate for the mm-sized bubbles. For significantly smaller bubbles, Equ. 1 must be modified to account for the effects of surface tension (See, T. G. Leighton, supra). The bubble resonance can be detected and quantified using a hollow cylindrical piezoelectric transducer surrounding the bubble.

After detachment from the nozzle, the bubble accelerates to its terminal velocity which depends on the size of the bubble. For low viscosity fluids, such as water, the behavior of the rising bubble falls within several regions. Small bubbles (less than 0.035 cm radius) are spherical and rise substantially vertically at a speed determined by Stokes' Law. Larger bubbles (0.035 cm to 0.07 cm), have internal air circulation, which reduces shear stresses at the interface leading to a velocity higher than predicted by Stokes' Law. Between 0.07 cm and 0.3 cm, bubbles are elliptical and follow a spiral or zigzag path. Drag increases due to vortex formation in the bubble wake. Bubbles greater than 0.3 cm form spherical cap shapes (See, e.g., L.-S. Fan and K. Tsuchiya, *Bubble Wake Dynamics in Liquids and Liquid-Solid Suspensions* (Butterworth-Heinemann, Boston, 1990), pp. 36–43.).

The terminal velocity $U_0$ depends on the buoyant and drag forces on the bubble (See, H. Kellerman et al., supra):

$$U_0 = \sqrt{\frac{8}{3}\frac{gR_0}{C_D}}, \qquad (2)$$

where g is the acceleration due to gravity, $R_0$ is the radius of the bubble and $C_D$ is the drag coefficient. The drag coefficient depends on physical properties of the liquid and the size of the bubble. A theory by G. Bozzano and M. Dente, "Shape and terminal velocity of single bubble motion: a novel approach," Computers & Chemical Engineering. 25 (2001) 571–576, is useful for calculating the drag coefficient because it covers a wide range of bubble sizes and liquid properties. The drag coefficient is calculated using Reynolds, Eotvos, and Morton numbers, which depend on the surface tension, density, and viscosity of the liquid and the bubble size. An equation for terminal velocity applicable for air bubbles between 0.07 cm and 0.3 cm is given by (See L.-S Fan and K. Tsuchiya, supra):

$$U_0 = \sqrt{\frac{c\sigma}{R_0 \rho}}, \quad (3)$$

where c=1.8 for a single component liquid (c is between 1.0 and 1.4 for mixtures). The presence of contaminants (e.g., surfactants, suspended particles) has a significant effect on the rise of the bubble due to the Marangoni effect and the immobilization of the air-liquid interface (See, e.g., G. Liger-Belair et al., "On the Velocity of Expanding Spherical Gas Bubbles Rising in Line in Supersaturated Hydroalcoholic Solutions: Application to Bubble Trains in Carbonated Beverages," Langmuir 16, 1889–1895 (2000).).

The path of the rising bubbles is largely determined by the Reynolds number, $N_R$. For low Reynolds numbers ($N_R$<130), the bubble travels substantially vertically. For higher Reynolds numbers (130<$N_R$<400), the tip of the wake behind the bubble becomes unstable and oscillates at a low frequency, leading to a zigzag path. For even higher Reynolds numbers (400<Re<350,000), vortices are periodically shed from alternate sides of the bubble on a plane that slowly revolves around the bubble, leading to a spiral path (See T. G. Leighton, supra).

As the mm-sized bubble rises, it also undergoes shape oscillations (P. Di Marco et al., supra). The frequency of these oscillations (See T. G. Leighton, supra) is given by:

$$f_n = \frac{1}{2\pi}\sqrt{(n-1)(n+1)(n+2)\frac{\sigma}{\rho R_0^3}}, \quad (4)$$

where $f_n$ is the frequency of oscillations, n is the mode number, and $\sigma$ is the surface tension.

Both terminal velocity and shape oscillations can be monitored by observing the Doppler frequency shift of sound reflected from the bubble. The speed, U, of the bubble is related to the speed of sound, the frequency of the sound source used to interrogate the bubble, and the frequency received by the detector utilized for the measurement according to:

$$U = v\frac{(f_r - f_s)}{(f_r + f_s)}, \quad (5)$$

where v is the liquid sound speed, $f_r$ is the received frequency, and $f_s$ is the source frequency (See, e.g., D. G. H. Andrews, "An experiment to demonstrate the principles and processes involved in medical Doppler ultrasound," Phys. Educ. 35(5), 350–353 (2000)).

Accordingly, it is an object of the present invention to provide an apparatus and method for measuring liquid characteristics from the properties of bubbles formed therein.

Additional objects, advantages and novel features of the invention will be set forth, in part, in the description that follows, and, in part, will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with its purposes of the present invention, as embodied and broadly described herein, the method for measuring liquid properties hereof includes: forming a bubble in the liquid; measuring the resonance frequency of the bubble; measuring the shape oscillation frequency of the bubble; and measuring the terminal velocity of the bubble in the liquid.

In another aspect of the invention and in accordance with its objects and purposes, the apparatus for measuring liquid properties hereof includes: means for forming a bubble in the liquid; means for measuring the resonance frequency of the bubble; means for measuring the shape oscillation frequency of the bubble; and means for measuring the terminal velocity of the bubble in the liquid.

Benefits and advantages of the present invention include, but are not limited to, the noninvasive, inexpensive measurement of liquid density, surface tension and viscosity, and the monitoring of changes in these quantities. It should be mentioned that the invention is applicable to opaque liquids. Moreover, by making simultaneous passive listening and active Doppler measurements on a bubble, all aspects of the bubble evolution (bubble formation, growth, detachment and resonance, shape oscillations, terminal velocity, and rise path) can be observed which permits liquid properties to be determined.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings:

FIG. 7a are Fourier transforms of bubble resonance signals for two air flows; while

FIG. 8a are Fourier transforms of bubble resonance signals when a surfactant is added to water compared with those for pure water; while

FIG. 9a are Fourier transform of bubble resonance signals resulting when isopropyl alcohol is added to water, compared with those for pure water; while

FIG. 10a are Fourier transforms of bubble resonance signals when particles are suspended in water compared with those for pure water; while

DETAILED DESCRIPTION

Briefly, the present invention includes a method for determining surface tension, density and viscosity of a liquid, and for monitoring changes in these characteristics by measuring the resonance frequency, terminal velocity and shape oscillation frequency for bubbles formed in the liquid under investigation. Bubbles are formed in the liquid using forced air flow from a syringe tip; however, it is anticipated that a cavitation process in the liquid induced by the application of ultrasound to the liquid can be used as well. Additionally, other gases can be employed to form bubbles in situations where the liquid is sensitive to oxygen.

From Eq. 1 hereinabove, it is seen that the resonance frequency of a bubble is related to γ which is the ratio of the specific heat of the gas at constant pressure to the specific heat thereof at constant volume, the value of which depends on the nature of the gas. For example, for monotomic gases, γ=1.67, for diatomic gases, γ=1.41, while for polyatomic gases γ=1.3. Therefore, the resonant frequency of the bubble will depend on the gas being used for its generation. The terminal velocity and the shape oscillation frequency for the bubble are not affected by the choice of gas.

Typically, when bubbles are generated using cavitation, the vapor inside the bubble will be the vapor of the liquid that is cavitating. However, if gas is dissolved in the liquid, a portion of this gas may enter the bubble. In fact, dissolved gases lower the threshold for cavitation. Additionally, under certain circumstances the identity of the dissolved gas can be determined from the resonance frequency.

As long as a consistent set of bubble measurements is used in the analysis in accordance with the present invention; that is, measurements taken using either the cavitation method or the syringe method for bubble formation, the above-mentioned properties of the liquid can be determined.

Although analytic algorithms are provided hereinbelow for extracting or monitoring the desired characteristics of the liquid from the three measured quantities, more general versions of Equations 1–4 can be parametrically solved numerically to extract these characteristics. The present method is not restricted to optically transparent liquids, and the quantities can be measured using technology found in references listed hereinabove.

One embodiment of the invention includes: (1) passive listening using acoustic technology to measure bubble resonance frequency; and (2) an active Doppler (Joint Time-Frequency Analysis) method to measure bubble terminal velocity and shape oscillation frequency. Since these quantities are affected by the physical properties of the surrounding liquid (that is, surface tension, density, viscosity), the liquid can be characterized and monitored from measurements on bubbles formed therein.

Equations (1)–(4) show the relationship of bubble resonance frequency, terminal velocity, and shape oscillation frequency to the surface tension and density of the host liquid. Rearranging these equations, the above physical properties of the liquid determined from observable quantities are as follows:

$$\rho = \frac{0.350 c f_n^2 p_0}{f_0^2 U_0^2} \tag{6}$$

$$R_0 = \frac{0.551 U_0}{f_s \sqrt{c}} \tag{7}$$

$$\sigma = \frac{0.193 f_n U_0 p_0}{f_0^2 \sqrt{c}} \tag{8}$$

For small bubbles, where Stokes' Law applies, the viscosity is inversely proportional to terminal velocity. Therefore, the viscosity of the liquid can also be determined from the terminal velocity, once the system is calibrated using a liquid having known viscosity (Calibration may not be necessary since viscosity can be determined from bubble resonance frequency and terminal velocity. Liquid viscosity η is inversely proportional to the product of square of the resonance frequency and the terminal velocity as η∝1/($f_0^2 U_0$)). The viscosity and the resonance frequency are the two measured parameters. Equation 9 below provides a more quantitative relationship among the measured parameters in order to experimentally determine viscosity $$\eta = \frac{0.0236 g p_0}{f_0^2 U_0}. \tag{9}$$

The parameters g, $p_0$, $f_0$, and $U_0$ are defined hereinabove.

The dynamics of bubble rise through any liquid is a function of bubble size which in turn depends on liquid properties such as density and surface tension. Equations (6)–(8) faithfully represent the behavior of bubbles having a range of sizes below a cut-off value. To provide a bubble size for comparison among various liquids, a dimensionless number called the Eotvos number is used. The Eotvos number takes into account liquid density and surface tension to normalize the bubble size. Although the above equations (which are used principally because of their simplicity of form) are strictly valid for liquids having an Eotvos number $\leq 50$, a large range of bubble sizes can be accommodated by numerically solving more general equations. The method of the present invention is expected to be useful for Eotvos numbers $\leq 50$. For water, this condition defines a bubble having a radius of approximately 7 mm.

Reference will now be made in detail to the present preferred embodiments of the invention examples of which are illustrated in the accompanying drawings. In what follows, identical callouts will be used for similar or identical structure.

Figure 1:
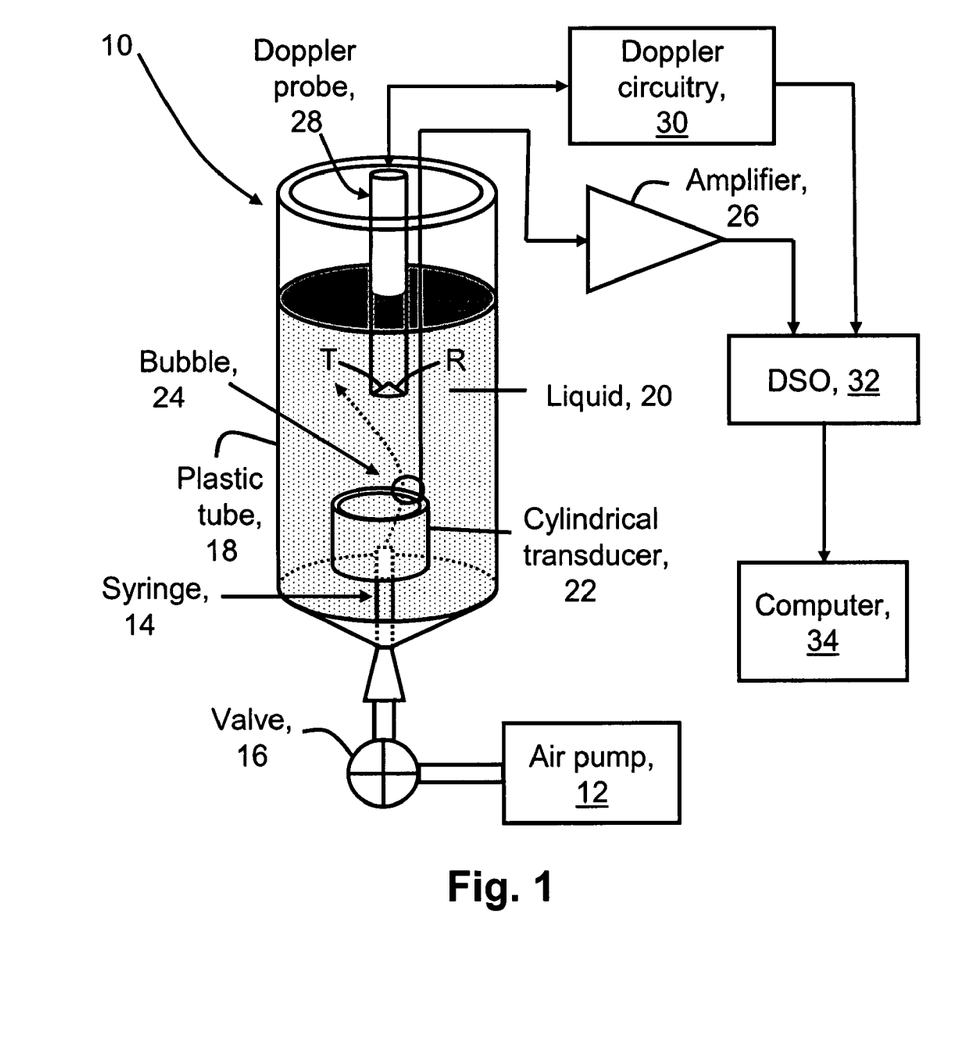
FIG. 1 is a schematic representation of the resonance-Doppler apparatus of the present invention showing a pump for injecting a gas into a chamber through a syringe needle, thereby producing a bubble; a cylindrical transducer disposed around the tip of the needle for detecting the sound generated both when the bubble forms and when it detaches; a Doppler probe disposed above the needle for monitoring the growth and rise of the bubble (T=transmitter, R=receiver); and a computer for analyzing the digitized output of both of these sensors.

Turning now to FIG. 1, hereof, a schematic representation of the apparatus, 10, used to demonstrate the present method is shown. In this embodiment of the invention, bubbles are generated by forcing air from air pump, 12, through metal syringe, 14. The flow-rate was adjustable both using valve, 16, and by changing the air pressure delivered by the pump. The syringe needle was inserted through the closed bottom portion of a vertically oriented plastic tube, 18, which served as the container for the liquids, 20, investigated. The tube was generally filled to 6 cm above the syringe needle, and measurements were made using water nominally at 20° C., the ambient room temperature. Clearly, bubbles can be formed using other gases, and the present apparatus can be used to investigate the associated liquid. The size of the orifice of the syringe is unimportant. Although the initial size of the bubble changes with orifice size, and the measured properties scale with the bubble size, so long as the bubble size is consistent with the discussion of the Eotvos number, hereinabove (as an example, for water, the bubble diameter should be less than about 7 mm), the liquid parameters derived from these measured properties are unaffected.

Hollow cylindrical piezoelectric transducer (2.55-cm long, 2.30-cm inner diameter, 1.20-mm thick, Boston Piezo-Optics, Mass.), 22, was disposed symmetrically around the tip of the syringe to enable detection of sound produced by bubble, 24, in many directions. Traditionally, such resonance measurements are made from one side using a hydrophone. The transducer output was amplified using amplifier, 26.

A frequency-mixing-based Doppler apparatus which includes Doppler probe, 28, controlled by Doppler circuitry, 30, was used to monitor the speed of ascending bubble 24 as a function of time. The outputs of both the cylindrical transducer and circuitry 30 were directed to a 2-channel, digital storage oscilloscope (DSO), 32, which digitized the data and transferred it to computer, 34, for analysis.

Figure 2:
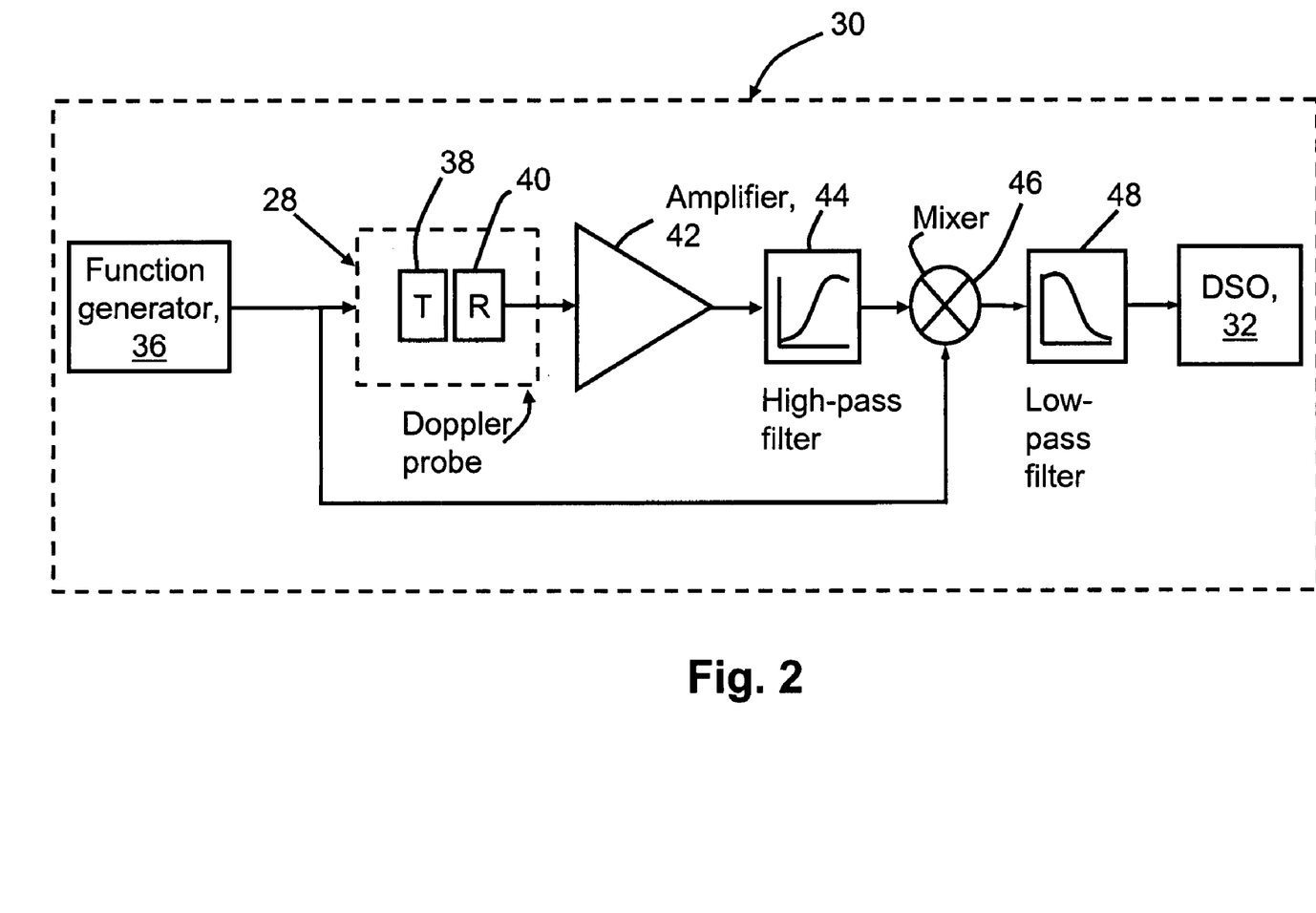
FIG. 2 is a schematic representation of an embodiment of the Doppler probe measurement electronics used in cooperation with the present resonance-Doppler apparatus, showing a local oscillator for exciting the transmitter of the Doppler probe at 10 MHz; an amplifier for amplifying the signal produced by the Doppler probe in response to the reflected sound from the rising bubble; a high-pass filter for reducing noise, the output therefrom being mixed with the local oscillator signal to produce sum and difference frequencies; and a low-pass filter for removing the sum frequency, leaving the difference, or Doppler, frequency.

Doppler circuitry 30 is schematically described in FIG. 2 hereof. Function generator, 36, provides ultrasonic excitation for transmitter, 38, of dual-element Doppler probe (9.4 MHz, 10-cm long, 9.5-mm diameter, Parks Medical Pencil Probe), 28, normally placed about 4 cm above the tip of syringe 14. Receiver, 40, of the Doppler probe 28 detects the sound reflected from ascending bubble 24. Amplifier, 42, and high-pass filter, 44, are used to process the signal received by receiver 40 before it is mixed with the signal input to transmitter 38 using mixer, 46, to produce sum and difference frequencies. Low-pass filter, 48, permits the Doppler difference frequency to be obtained from the mixer. It is this difference frequency that is related to the bubble velocity and shape oscillations as will be discussed hereinbelow. Doppler probe 28 is shown in FIG. 1 hereof to include a pair of tilted transducers which are angled downwards (38, 40) to monitor the ascent of the bubbles; the probe utilized was a commercially available medical Doppler transducer probe designed for viewing veins under close-focusing conditions.

Figure 3:
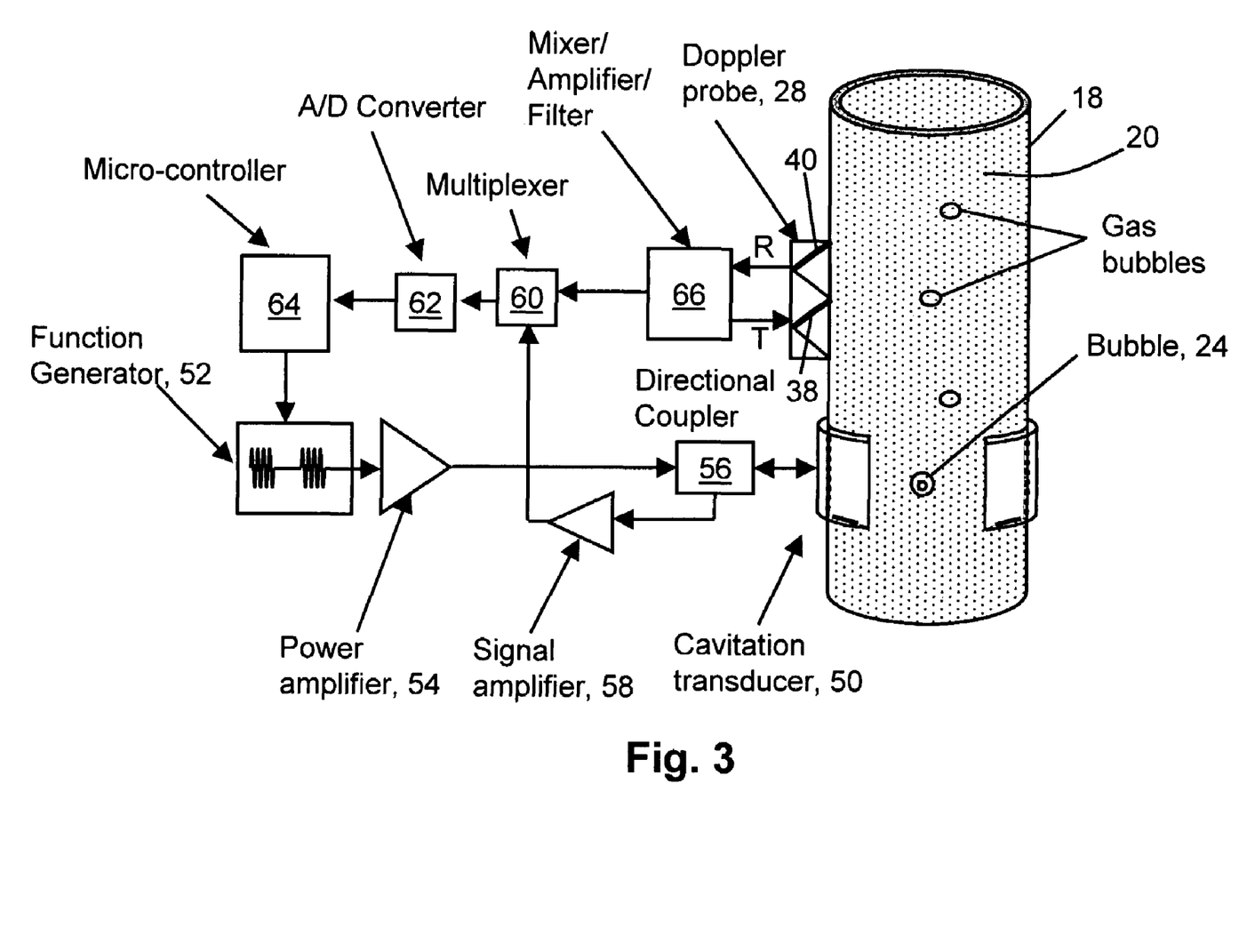
FIG. 3 is a schematic representation of a noninvasive embodiment of the resonance-Doppler apparatus of the present invention showing a piezoelectric ring (section) transducer disposed externally to a pipe or container bearing the liquid for generating focused, high intensity sound coaxially with the pipe and having sufficient intensity to generate bubbles, one at a time, by a cavitation process in the liquid; a function generator for producing tone bursts of sine-waves having a frequency matching the thickness mode resonance of the wall of the container; and an externally located Doppler probe for measuring the rate of ascent of the bubbles formed.

FIG. 3 hereof is a schematic representation of a noninvasive embodiment of the resonance-Doppler method of the present invention. In this embodiment, both the bubble generation and bubble detection are achieved externally to the pipe or cylindrical container bearing the liquid under investigation. Piezoelectric ring transducer, 50, which can either be a complete ring or two half-rings that are in electrical connection is used to generate high intensity sound at the center and on the axis of the pipe. The curvature of the container focuses sound at the axis of the container. Function generator, 52, produces tone bursts of sine-waves having a frequency that matches the thickness mode resonance of the wall of the container.

Frequency matching permits the sound to be transmitted through the wall with the maximum efficiency. The frequency used can be either at the fundamental frequency or higher harmonics of the wall thickness mode resonance frequency. A broad range of acoustic frequencies can be used, but sound transmission through the wall may vary. The burst frequency, duration, and duty cycle can be adjusted for a chosen bubble generation rate. The output of the function generator is amplified by power amplifier, 54, before being applied to the transducer. By adjusting the power, frequency, burst duration, and duty cycle it is also possible to create a single bubble in the liquid inside the pipe or container by the cavitation process (See, e.g., T. G. Leighton, *The Acoustic Bubble* (Academic Press, London, 1994), 504–506).

Passive or active circuit directional coupler, 56, allows the same transducer to be used for both generating bubbles by cavitation, and for detecting the bubble resonance. The bubble resonance signal detected by cavitation transducer 50 is amplified by signal amplifier, 58, before being directed to multiplexer, 60, and digitized using A/D converter, 62. The resonance signal is generated when the burst signal is off. Microcontroller, 64 controls function generator 52 and multiplexer 60 as well as processing the signals received from both Doppler probe 28 and cavitation transducer 50.

The tilt of elements 38 and 40 of Doppler probe 28 shown in FIG. 1, hereof is not a requirement of the present invention; rather, a flat-surfaced, concentric transducer head having an outer ring surrounding an inner disk, where one transducer serves as the transmitter and the other as a receiver, will provide a symmetric sound beam pattern without focusing. This permits a longer viewing range for the bubble; that is, the received signal has been observed by the present inventor to be strong along the entire path of the bubble instead of only in the focused beam intersection region of the two tilted transducers.

The transducers for noninvasive measurements are acoustically coupled to the wall (a coupling medium can be employed to improve the acoustic coupling), and the resulting sound waves are directed (refracted) at an angle into the liquid inside. The Doppler probe frequency can be chosen to match a higher harmonic of the wall resonance frequency, allowing maximum sound transmission. The Doppler frequency is chosen to be greater than 5 MHz and, more typically, it is above 10 MHz. The received signal from the cavitation transducer, and the amplified output from mixer/amplifier/filter, 66, are directed through multiplexer 60 to A/D converter 62 before entering microcontroller 64 for signal processing. The microcontroller is capable of performing rapid Fast Fourier Transform (FFT) and Short-Time Fourier Transform (STFT) calculations using the bubble resonance signal and the Doppler signal as will be described in more detail hereinbelow.

The bubble resonance signal from the cylindrical transducer (as shown in FIG. 1 hereof) was transformed using FFT to obtain the frequency spectrum of the resonance of the bubble. The Doppler signal, by contrast, was analyzed using Joint Time-Frequency Analysis (JTFA), which is a technique in which the frequency components of a signal are displayed as a function of time. As result, signal changes, such as a time-dependent Doppler frequency, can be observed, thereby permitting the speed of the bubble to be determined as a function of time during the period of growth and rise. JTFA was performed using either the Short-Time Fourier Transform method (STFT) or the Continuous Wavelet Transform (CWT) procedure (See, e.g., S. Qian and D. Chen, *Joint Time-Frequency Analysis*. (Prentice Hall PTR, Upper Saddle River, 1996), pp. 45–52), both of which gave the same time-dependent velocity information.

Measurements were made at various temperatures, airflow rates, liquid heights, and transducer positions. Water temperature was measured using a digital thermometer with a 0.1° C. resolution. The effect of liquid height was evaluated by changing the amount of liquid in the container. Doppler measurements were performed at various probe heights above the syringe (See FIG. 1 hereof). A height of ~2.5 cm was used to study bubble formation, whereas a height of ~10 cm was used to study the ascent path of the bubble.

The effect of liquid contaminants was also examined. To determine the effects of surfactant contaminants, a 1% solution (by volume) of dishwashing soap in water was used. Solutions of isopropyl alcohol and water at various concentrations (with the highest concentration being 66% water, 34% alcohol by volume) were used to investigate the effect of organic chemical contaminants on the bubbles. A dilute suspension (~1 g/L) of turmeric particles (10 to 100 $\mu$m, having irregular shapes) in water was used to investigate the effect of suspended particles on bubble behavior. Turmeric was chosen because it provided a stable suspension.

Figure 4A:
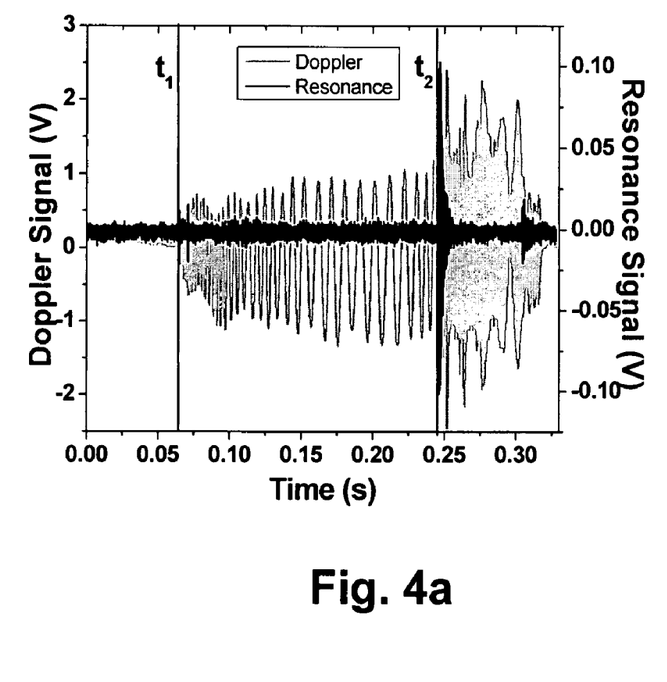
FIG. 4a illustrates signals detected during the evolution of a bubble, the black line representing the initial resonance signal detected by the cylindrical transducer, and the grey line representing the signal from the Doppler probe, the bubble forming at the tip of the needle at $t_1$, growing until $t_2$ when it detaches from the needle, rising and ultimately reaching terminal velocity.
Figure 4B:
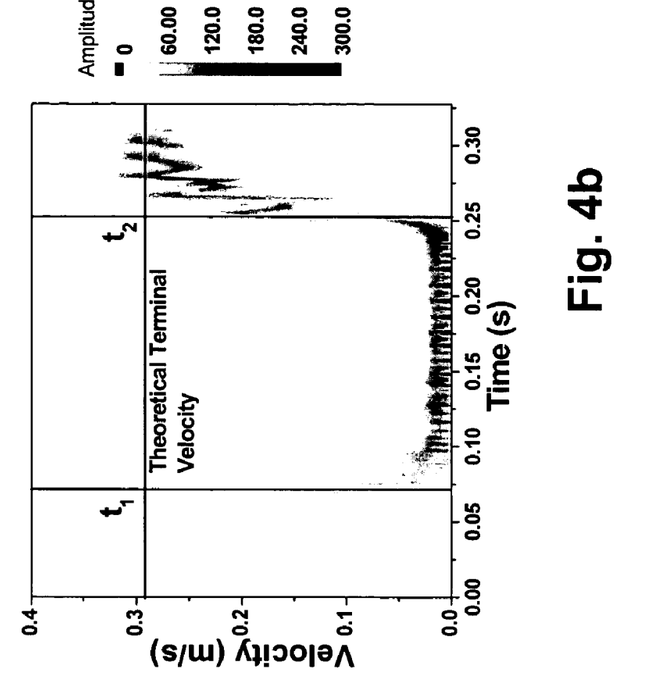
FIG. 4b shows the bubble velocity as a function of time.

Turning now to the measurements made in accordance with the present invention, FIG. 4a shows the signals from the cylindrical transducer and Doppler probe, whereas FIG. 4b shows the STFT of the Doppler signal, expressed as bubble velocity, which is proportional to the measured frequency difference. The measurement was made with the Doppler probe located 2.5 cm above the syringe. At time $t_1$, a small spike in the resonance signal (cylindrical transducer output) was observed, which is most likely due to a meniscus forming at the tip of the syringe (FIG. 4a). From time $t_1$ to time $t_2$, the bubble enlarged on the tip of the syringe. The growth process commenced with a rapid expansion of the bubble upward followed by horizontal growth. This was observed in the Doppler signal as an initial speed of 0.1 m/s at $t_1$ which decreased to 0.05 m/s. At $t_2$ the bubble detaches and begins to resonate, as indicated by a rapid increase in the speed (higher frequency Doppler signal) and an associated burst in the resonance signal. After $t_2$ the bubble accelerated to its terminal velocity while undergoing shape oscillations as observed by the oscillations in the STFT signal in FIG. 4b. The shape oscillation frequency has been observed to remain constant over time unless the properties of the liquid change with height; for example, if the liquid is stratified it may have a density gradient which varies as a function of height. In this situation, one would observe a variation in the shape oscillation frequency and the terminal velocity of the bubble.

Figure 6:
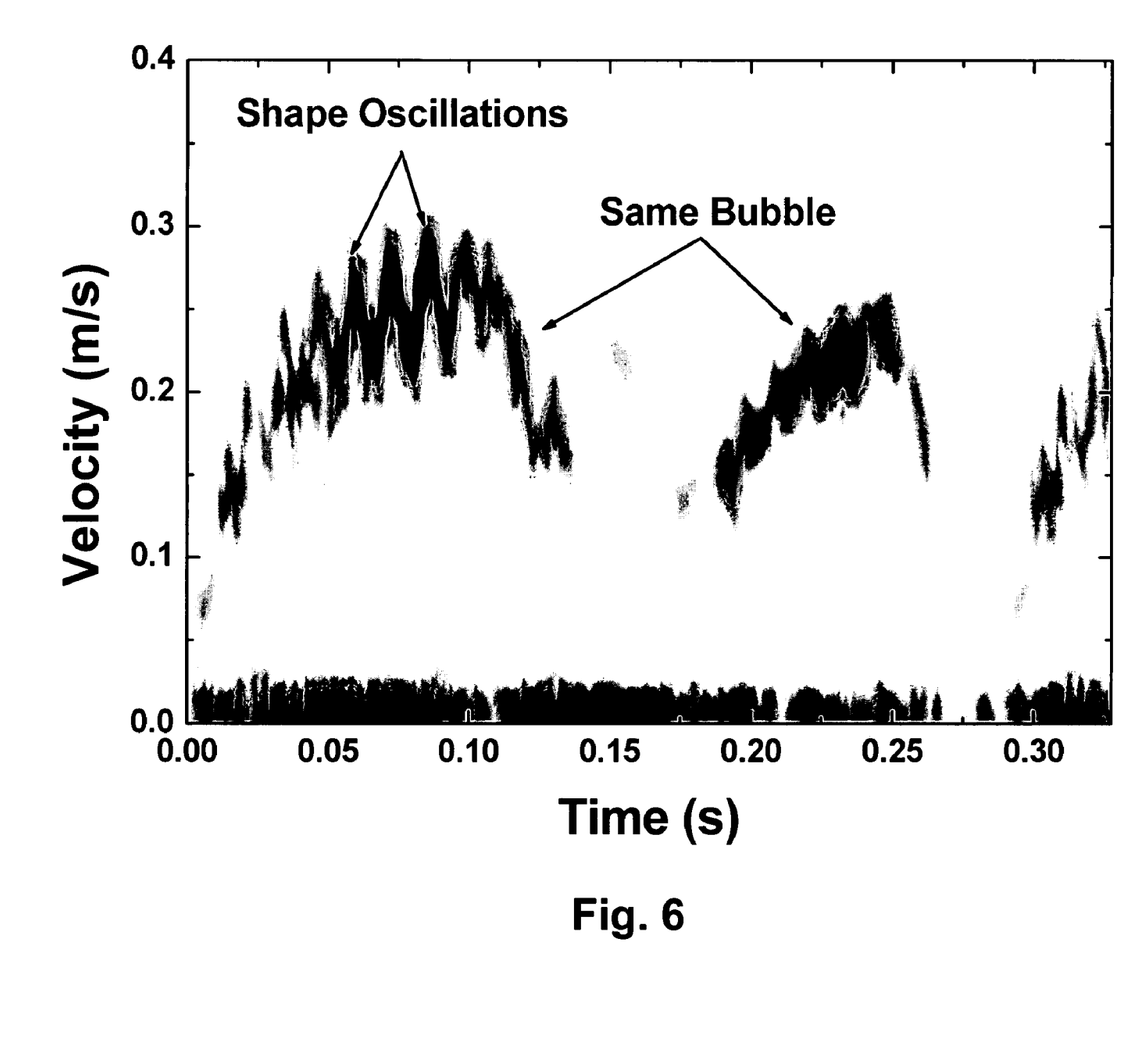
FIG. 6 is a long pathlength Doppler measurement for a single bubble rising in a spiral path.

With the exclusion of FIG. 6, the graphs labeled with (a) in the following figures show FFTs of the signal from the cylindrical transducer, whereas the graphs labeled with (b) show STFTs of the Doppler signal. The STFT is shown as a two-dimensional plot of velocity over time, with the degree of darkness indicating the magnitude of the Doppler signal.

The Resonance-Doppler measurements in the narrow temperature range studied (between 0° C. and 8° C.), show only a small effect of temperature on the bubble behavior (i.e., formation, growth, resonance, and rise).

Figure 5A:
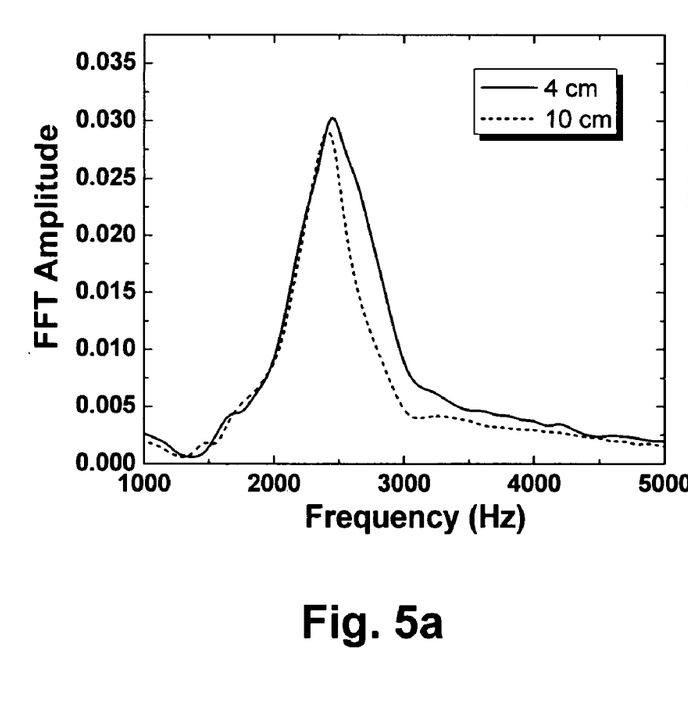
FIG. 5a shows the Fourier transform of a bubble resonance signal for two different water heights.
Figure 5B:
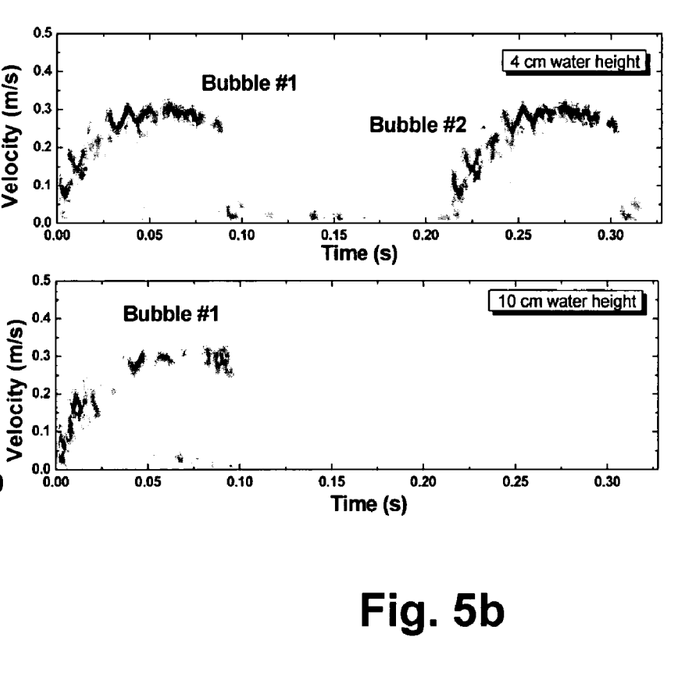
FIG. 5b shows the bubble velocity as a function of time for the two heights.

FIG. 5 shows that an increase in water height decreases the bubbling rate and the width of the resonance. These changes are due to the differences in the hydrostatic pressure.

As stated, the two transducers of the medical Doppler probe employed were slightly angled towards each other, which resulted in a focused beam directed below the probe (T and R in FIG. 1). Therefore, the probe detects the ascending bubble in a region directly below it. When the probe was positioned close to the tip of the syringe (e.g., about 4 cm), only the formation of the bubble and the start of its ascent can be adequately observed. When the probe at was located at approximately 10 cm, later periods of the ascent were found to be observable, including the nature of the rise path (e.g., straight, zigzag, or spiral). FIG. 6 shows how a spiral ascent path of the bubble affects the STFT data. For example, the oscillations in the velocity and the variations in the amplitude of the STFT of the Doppler signal (darkness of the plot) are due to the bubble moving in and out of the beam of the Doppler probe. A flat, concentric arrangement of the transducer elements having greater beam spread was also used, allowing more of the bubble's ascent to be observed (See FIG. 6 hereof).

Figure 7A:
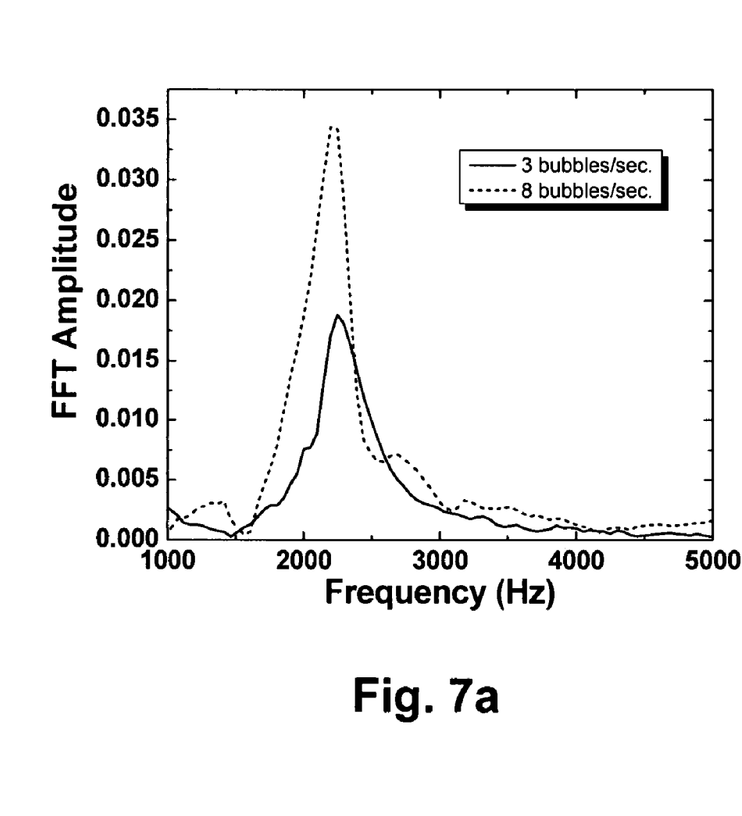
Figure 7B:
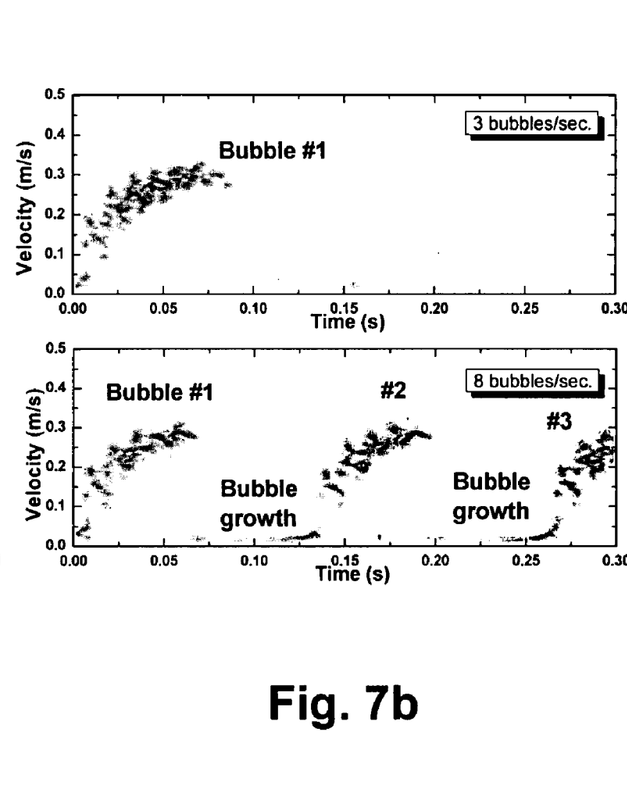
FIG. 7b shows the bubble velocity as a function of time for the two flow rates of FIG. 7a hereof.

As the flow rate of air increases, the bubble size remains relatively constant, as indicated by the fact that the resonance frequency does not change. At greater airflow rates, the bubble resonance is larger in amplitude (FIG. 7a), probably due a stronger axial jet from a faster detachment from the nozzle (See T. G. Leighton and A. J. Walton, supra). Moreover, the number of bubbles released per second increases, as is observed by the increased number of bubble detachments in a given length of time (FIG. 7b).

Figure 8A:
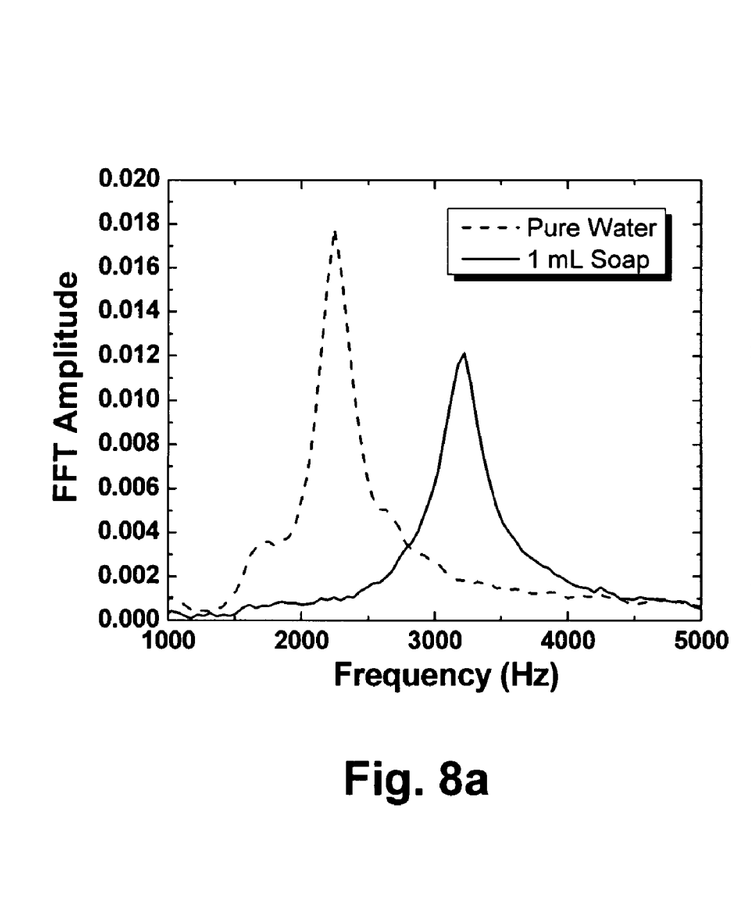
Figure 8B:
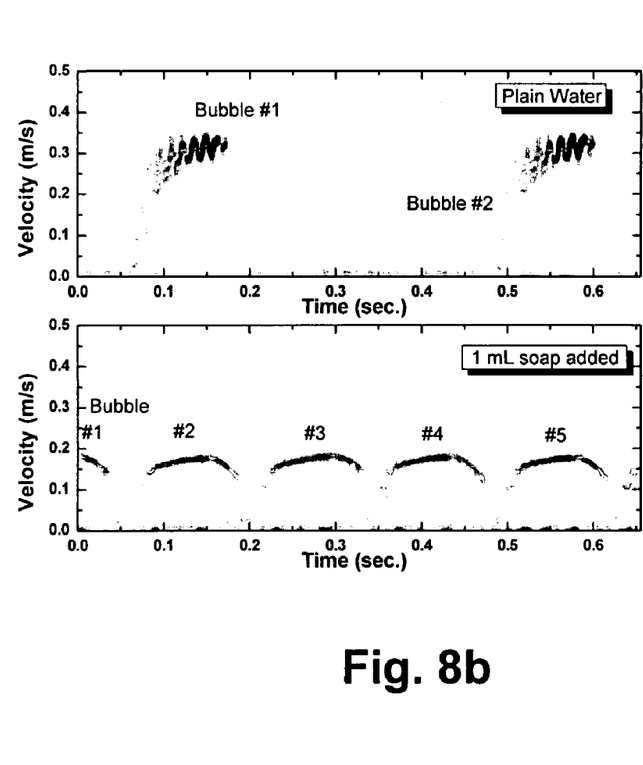
FIG. 8b shows the bubble velocity as a function of time for the two liquids.

The presence of surfactant was found to have a pronounced effect on many aspects of the evolution of the bubbles. For example, the bubble resonance moves to a higher frequency and becomes more damped (FIG. 8a). The increase in the resonance frequency is due to the smaller size of the bubbles (see Eq. 1). The bubbles are smaller in the soap solution than in plain water since they detach sooner because of the lower surface tension. Other effects include the following: the terminal velocity was less than half of the terminal velocity in pure water, the bubbling rate increased by greater than a factor of two, and the shape oscillations became too small to be easily determined (FIG. 8b). These observations are likely due to the presence of surfactant molecules at the air-liquid interface. The increase in resonance peak width is likely due to the higher viscosity of the soap solution.

Figure 9A:
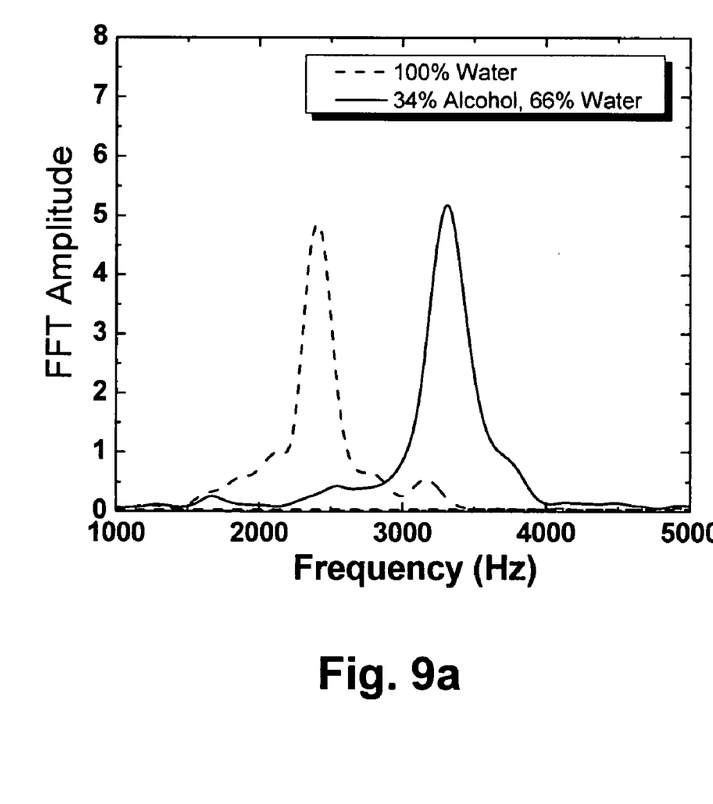
Figure 9B:
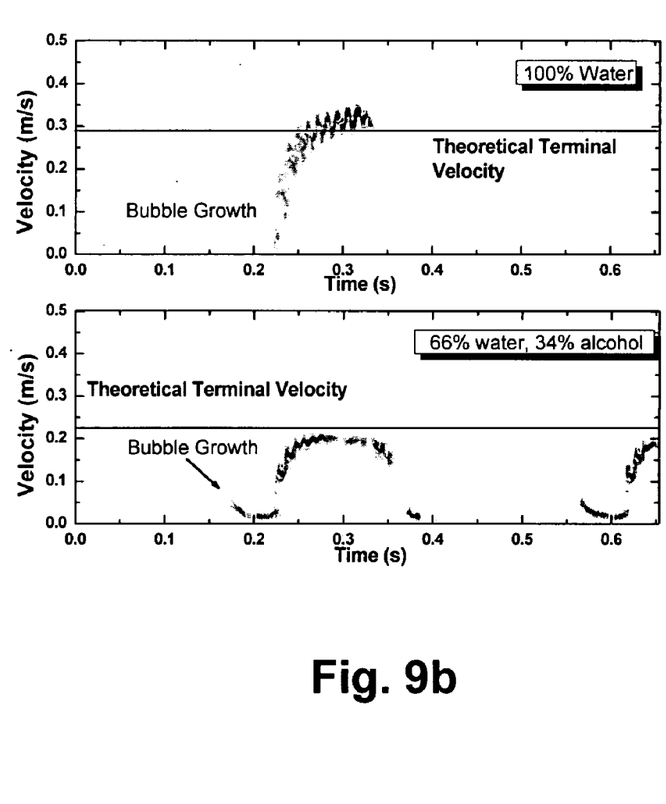
FIG. 9b shows the bubble velocity as a function of time for the two liquids.

Other contaminants, such as alcohol, also have a substantial change on the bubble's evolution. For example, the presence of isopropyl alcohol shifts the resonance peak to a higher frequency and increases the damping (FIG. 9a). In addition, the terminal velocity is significantly reduced, the bubbling rate increases, and the shape oscillations becomes smaller (FIG. 9b). The period of bubble growth is also shorter, showing that the bubbles detach from the nozzle sooner. These effects are very similar to those observed with the surfactant. This is likely due to the fact that both alcohol and soap lower the surface tension of the water, and the higher viscosity of the isopropyl alcohol concentration leads to a wider resonance peak width.

Figure 10A:
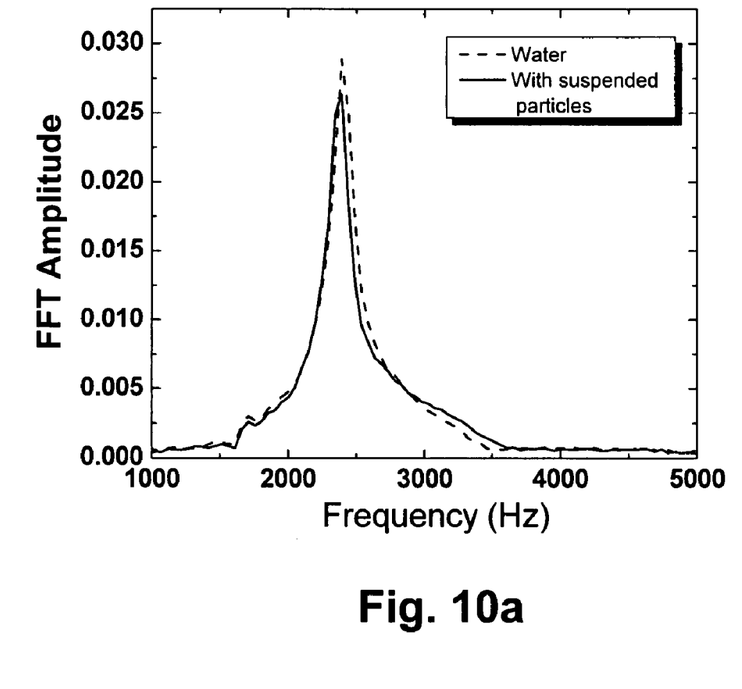
Figure 10B:
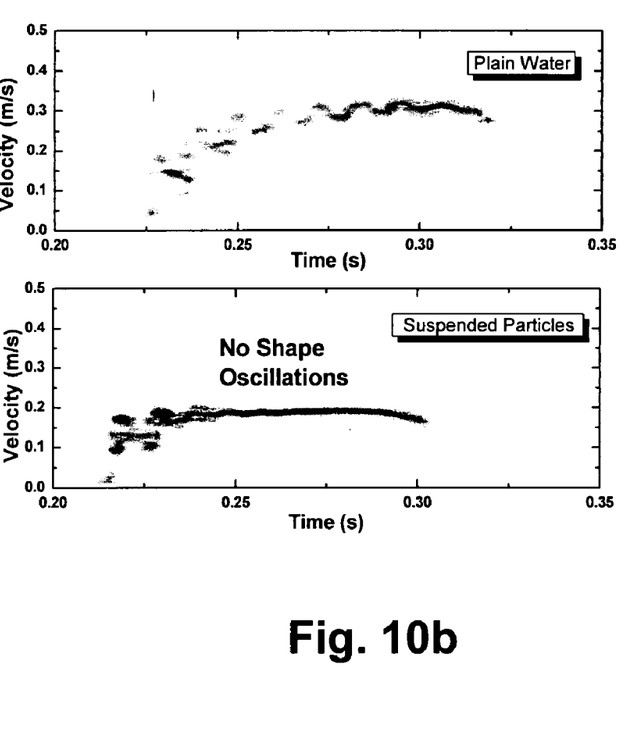
FIG. 10b shows the bubble velocity as a function of time for the two liquids.

FIG. 10 shows the effect of suspended particles (turmeric), in water. The suspended particles have little observable effect on the resonance of the bubble (FIG. 10a); however, the rise is affected. Instead of traveling along a wide spiral path upwards, as in the case of uncontaminated water, it was observed that the bubbles follow a tight spiral around the axis of the cylindrical test chamber. Moreover, the shape oscillations decay rapidly becoming too small to measure. These changes likely occur because the suspended particles adhere to the air-water interface of the bubble, thereby stiffening the boundary and increasing the effective viscosity (See L.-S. Fan and K. Tsuchiya, supra)

TABLE 1 summarizes the experimental results of various aspects of bubble dynamics and compares some of the results with theoretical predictions.

TABLE 1

| | Bubble Radius (mm) | Shape oscillation Freq. (Hz) | Terminal velocity (m/s) | Bubbling rate (bub./s) |
|---|---|---|---|---|
| Water (Exp.) | 1.44 ± 0.05 | 86.7 ± 5.5 | 0.311 ± 0.009 | ~2 |
| (Theor. Pred.) | 1.23 | 92.6 | 0.295 | — |
| Alcohol (Exp.) | 1.05 ± 0.02 | 100 ± 9.5 | 0.192 ± 0.008 | ~4 |
| (Theor. Pred.) | 1.00 | 104 | 0.228 | N/A |
| Soap (Exp.) | 1.12 ± 0.09 | None | 0.190 ± 0.006 | ~6 |
| Turmeric (Exp.) | 1.42 ± 0.07 | None | 0.248 ± 0.051 | ~2 |

Equation 1 is used to calculate the experimental bubble size from its resonance frequency. For theoretical predictions of bubble size, see e.g., M. S. Longuet-Higgins et al., supra, which describes bubble formation at low flow rates. This is not the situation for the present measurements, which may be the cause for the observed differences between the theoretical and the measured bubble sizes.

The frequency of the shape oscillations in the time-frequency plots is determined by averaging the period of four oscillations and taking the reciprocal. The theoretical frequencies (Eq. 3) are determined for a second-order (n=2, ellipsoidal) oscillation and agree well with experimental values for water and the alcohol/water mixture. The alcohol/water mixture shows a higher shape oscillation frequency because of the smaller bubble radius as compared with plain water. No shape oscillations could be easily discerned with the other contaminants.

The theory by G. Bozanno and M. Dente, supra, was used to determine the drag coefficient from the terminal velocity, which is in turn used in Eq. (2). The decrease in the terminal velocity of the isopropyl alcohol/water mixture is consistent with theory (smaller bubble radius).

Thus, by measuring the evolution of the bubble (bubble resonance, terminal velocity, and shape oscillations), certain physical properties of the liquid can be measured and monitored. For example, surface tension can be determined from the bubble radius, which is in turn derived from the resonance frequency and shape oscillation measurements (Eqs. 1 and 3). The predicted values were 74 mN/m for water (actual=72.9 mN/m) and 36 mN/m for the alcohol/water mixture (actual=27.4 mN/m). However, this method is applicable only if the liquid density is known.

Without prior knowledge of the physical properties of the liquid, if the resonance frequency, shape oscillation frequency, and terminal velocity of the bubble are measured, and Eqs. (6)–(8) hereof employed, the liquid surface tension and density (and bubble size) can be determined. This is demonstrated for the case of water and a water-isopropanol mixture in TABLE 2. The calculated values agree well with measured values reported in the literature. The equation for terminal velocity, Eq. (3), applies for high Reynolds numbers ($450 < N_R < 1900$), so accurate values for the other liquids were not obtained. A more general equation for terminal velocity may allow extraction of physical parameters for a wide range of liquids. However, by using smaller bubbles ($N_R < 1$), which obey Stokes' Law (See L.-S. Fan and K. Tsuchiya, supra), it should be possible to determine viscosity as well by simply measuring the bubble resonance frequency and the terminal velocity (see Eq. 9).

TABLE 2

| Liquid | Observable Parameter | Calculated Value | Literature Value |
|---|---|---|---|
| Water (c = 1.8) | $f_n$ = 86.7 Hz | $\rho$ = 0.988 ± 0.039 g/cm$^3$ | $\rho$ = 1.00 g/cm$^3$ |
| | $f_0$ = 2273 Hz | $R_0$ = 1.465 ± 0.038 mm | N/A |
| | $U_0$ = 0.311 m/s | $\sigma$ = 77.0 ± 1.5 mN/m | $\sigma$ = 72.9 mN/m |
| Isopropyl alcohol/ Water mixture (c = 1.0) | $f_n$ = 100.3 Hz | $\rho$ = 0.931 ± 0.13 g/cm$^3$ | $\rho$ = 0.940 g/cm$^3$ |
| | $f_0$ = 3249 Hz | $R_0$ = 0.963 ± 0.08 mm | N/A |
| | $U_0$ = 0.192 m/s | $\sigma$ = 36.0 ± 0.955 mN/m | $\sigma$ = 27.38 mN/m |

The bubble resonance width also provides a quantitative measure of the viscosity. If the present apparatus is calibrated using a liquid having known viscosity, the resonance width can provide liquid viscosity information.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for measuring properties of a liquid which comprises:
   forming a bubble in the liquid;
   measuring the resonance frequency of the bubble;
   measuring the shape oscillation frequency of the bubble;
   measuring the terminal velocity of the bubble in the liquid; and
   determining the liquid property or properties from the measured resonance frequency of the bubble, the shape oscillation frequency of the bubble, and the terminal velocity of the bubble.

2. The method as described in claim 1, wherein said step of forming the bubble in the liquid is achieved by passing a chosen gas through a nozzle located within the liquid.

3. The method as described in claim 1, wherein the chosen gas comprises air.

4. The method as described in claim 2, wherein said step of measuring the resonance frequency of the bubble in the liquid is achieved using passive ultrasonic detection of the resonance frequency of the bubble after it detaches from the nozzle.

5. The method as described in claim 2, wherein said step of measuring the shape oscillation frequency of the bubble is performed by measuring the Doppler frequency shift of the ascending bubble.

6. The method as described in claim 5, further comprising the step of applying Joint Time Frequency Analysis to the Doppler frequency shift of the ascending bubble.

7. The method as described in claim 5, wherein said the step of measuring the shape oscillation frequency of the bubble is performed by measuring the acoustic Doppler frequency shift of the ascending bubble of the ascending bubble.

8. The method as described in claim 2, wherein said step of measuring the terminal velocity of the bubble is performed by measuring the Doppler frequency shift of the ascending bubble.

9. The method as described in claim 8, further comprising the step of applying Joint Time Frequency Analysis to the Doppler frequency shift of the ascending bubble.

10. The method as described in claim 8, wherein said the step of measuring the shape oscillation frequency of the bubble is performed by measuring the acoustic Doppler frequency shift of the ascending bubble.

11. The method as described in claim 1, wherein the properties of the liquid comprise surface tension, viscosity and density.

12. A method for measuring properties of a liquid which comprises:
   forming a bubble in the liquid by cavitation;
   measuring the resonance frequency of the bubble;
   measuring the shape oscillation frequency of the bubble;
   measuring the terminal velocity of the bubble in the liquid; and
   determining the liquid property or properties from the measured
   resonance frequency of the bubble, the shape oscillation frequency of the
   bubble, and the terminal velocity of the bubble.

13. The method as described in claim 12, wherein said step of forming the bubble in the liquid by cavitation is achieved by applying acoustic energy to the liquid.

14. The method as described in claim 12, wherein said step of measuring the resonance frequency of the bubble in the liquid is achieved using passive ultrasonic detection of the resonance frequency of the bubble.

15. The method as described in claim 12, wherein said step of measuring the shape oscillation frequency of the bubble is performed by measuring the Doppler frequency shift of the ascending bubble.

16. The method as described in claim 15, further comprising the step of applying Joint Time Frequency Analysis to the Doppler frequency shift of the ascending bubble.

17. The method as described in claim 12, wherein said the step of measuring the shape oscillation frequency of the bubble is performed by measuring the acoustic Doppler frequency shift of the ascending bubble.

18. The method as described in claim 12, wherein said step of measuring the terminal velocity of the bubble is performed by measuring the Doppler frequency shift of the ascending bubble.

19. The method as described in claim 18, further comprising the step of applying Joint Time Frequency Analysis to the Doppler frequency shift of the ascending bubble as a function of time.

20. The method as described in claim 12, wherein said the step of measuring the terminal velocity of the bubble is performed by measuring the acoustic Doppler frequency shift of the ascending bubble of the ascending bubble.

21. The method as described in claim 12, wherein the properties of the liquid comprise surface tension, viscosity and density.

22. An apparatus for measuring properities of a liquid which comprises:
   means for forming a bubble in the liquid;
   means for measuring the resonance frequency of the bubble;
   means for measuring the shape oscillation frequency of the bubble;
   means for measuring the terminal velocity of bubble as it ascends in the liquid; and
   means for determining the liquid property or properities from the measured resonance frequency of the bubble, the shape oscillation frequency of the bubble, and the terminal velocity of the bubble.

23. The apparatus as described in claim 22, wherein said means for forming the bubble in the liquid comprises a nozzle located within the liquid through which a chosen gas is passed.

24. The apparatus as described in claim 23, wherein the chosen gas comprises air.

25. The apparatus described in claim 22, wherein said means for measuring the resonance frequency of the bubble in the liquid comprises a passive ultrasonic detector.

26. The apparatus as described in claim 22, wherein said means for measuring the shape oscillation frequency of the bubble comprises apparatus for measuring the Doppler frequency shift of the ascending bubble.

27. The apparatus as described in claim 26, wherein said means for measuring the shape oscillation frequency of the bubble further comprises means for applying Joint Time Frequency Analysis to the Doppler frequency shift of the ascending bubble.

28. The apparatus as described in claim 22, wherein said means for measuring the shape oscillation frequency of the bubble comprises apparatus for measuring the acoustic Doppler frequency shift of the ascending bubble.

29. The apparatus as described in claim 22, wherein said means for measuring the terminal velocity of the bubble comprises apparatus for measuring the Doppler frequency shift of the ascending bubble.

30. The apparatus as described in claim 29, further comprising means for applying Joint Time Frequency Analysis to the Doppler frequency shift of the ascending bubble.

31. The apparatus as described in claim 22, wherein said means for measuring the shape oscillation frequency of the bubble comprises apparatus for measuring the acoustic Doppler frequency shift of the ascending bubble.

32. The method as described in claim 22, wherein the properties of the liquid comprise surface tension, viscosity and density.

33. An apparatus for measuring properities of a liquid which comprises:
   cavitation means for forming abubble in the liquid;
   means for measuring the resonance frequency of the bubble;
   means for measuring the shape oscillation frequency of the bubble;
   means for measuring the terminal velocity of the bubble as it ascends in the liquid; and
   means for determining the liquid property or properties from the measured resonance frequency of the bubble, the shape oscillation frequency of the bubble, and the terminal velocity of the bubble.

34. The apparatus as described in claim 33, wherein said cavitation means comprises apparatus for applying acoustic energy to the liquid.

35. The apparatus as described in claim 33, wherein said means for measuring the resonance frequency of the bubble in the liquid comprises apparatus for passive ultrasonic detection of the resonance frequency of the bubble.

36. The apparatus as described in claim 35, wherein said means for measuring the resonance frequency of the bubble in the liquid comprises apparatus for passive ultrasonic detection of the resonance frequency of the bubble, and for applying acoustic energy to the liquid.

37. The apparatus as described in claim 33, wherein said means for measuring the shape oscillation frequency of the bubble comprises apparatus for measuring Doppler frequency shift of the ascending bubble.

38. The apparatus as described in claim 37, further comprising means for applying Joint Time Frequency Analysis to the Doppler frequency shift of the ascending bubble.

39. The apparatus as described in claim 33, wherein said means for measuring the shape oscillation frequency of the bubble comprises apparatus for measuring the acoustic Doppler frequency shift of the ascending bubble.

40. The apparatus as described in claim 33, wherein said means for measuring the terminal velocity of the bubble comprises apparatus for measuring the Doppler frequency shift of the ascending bubble.

41. The apparatus as described in claim 40, further comprising means for applying Joint Time Frequency Analysis to the Doppler frequency shift of the ascending bubble as a function of time.

42. The apparatus as described in claim 33, wherein said means for measuring the terminal velocity of the bubble comprises apparatus for measuring the acoustic Doppler frequency shift of the ascending bubble.

43. The apparatus as described in claim 33 wherein the properties of the liquid comprise surface tension, viscosity and density.

* * * * *